(12) United States Patent
Kindler et al.

(10) Patent No.: US 8,952,186 B2
(45) Date of Patent: Feb. 10, 2015

(54) METHOD FOR DEHYDRATING A CARBOHYDRATE-COMPRISING

(75) Inventors: Alois Kindler, Grünstadt (DE); Klemens Massonne, Bad Dürkheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/528,983

(22) Filed: Jun. 21, 2012

(65) Prior Publication Data

US 2012/0330039 A1 Dec. 27, 2012

Related U.S. Application Data

(60) Provisional application No. 61/499,715, filed on Jun. 22, 2011.

(51) Int. Cl.
C07D 307/50 (2006.01)
C07D 307/46 (2006.01)

(52) U.S. Cl.
CPC .................................. C07D 307/46 (2013.01)
USPC ......................................... 549/488; 549/489

(58) Field of Classification Search
CPC .................................................... C07D 307/46
USPC ................................................. 549/488, 489
See application file for complete search history.

(56) References Cited

U.S. PATENT DOCUMENTS

| | | | |
|---|---|---|---|
| 3,201,331 A * | 8/1965 | Hunter | 203/64 |
| 2004/0073035 A1 | 4/2004 | Maase et al. | |
| 2005/0020807 A1 * | 1/2005 | Boon et al. | 528/481 |
| 2010/0081798 A1 | 4/2010 | Balensiefer et al. | |
| 2010/0112646 A1 | 5/2010 | Balensiefer et al. | |
| 2011/0275868 A1 | 11/2011 | Prochazka et al. | |
| 2011/0275869 A1 | 11/2011 | Prochazka et al. | |
| 2012/0270033 A1 | 10/2012 | Granstr m et al. | |

FOREIGN PATENT DOCUMENTS

| | | |
|---|---|---|
| DE | 102 02 838 A1 | 8/2003 |
| EP | 0217280 A1 | 4/1987 |
| EP | 0376182 A1 | 7/1990 |
| EP | 2145872 A1 | 1/2010 |
| JP | 2003104929 A | 4/2003 |
| WO | WO-0240426 A2 | 5/2002 |
| WO | WO-2006063220 A2 | 6/2006 |
| WO | WO-2008053284 A1 | 5/2008 |
| WO | WO-2008090155 A1 | 7/2008 |
| WO | WO-2008090156 A1 | 7/2008 |
| WO | WO 2009030511 A1 * | 3/2009 |

OTHER PUBLICATIONS

Moreau, C., Dehydration of fructose and sucrose into 5-hydroxymethylfurfural in the presence of 1-H-3-methyl imiazolium chloride activing as both solvent and catalyst, 2006, J. Mol. Catal. A: Chemical 253: 165-169.*
Qi, X., Efficient Calalytic Conversion of Fructose into 5-hydroxymethylfurfural in Ionic Liquids at Room Temperature, 2009, ChemSusChem 2: 944-946.*
International Search Report for PCT/EP2012/061909.
Kabyemela, et al. "Kinetics of Glucose Epimerization and Decomposition in Subcritical and Supercritical Water", Ind. Eng. Chem., Res., vol. 36 (1997), pp. 1552-1558.
Written Opinion of International Searching Authority for PCT/EP2012/061909.
U.S. Appl. No. 61/321,154.
U.S. Appl. No. 61/387,024.
U.S. Appl. No. 13/512,637.
U.S. Appl. No. 13/530,890.
Corma, et al., "Chemical Routes for the Transformation of Biomass into Chemicals", Chem. Rev., vol. 107, (2007), pp. 2411-2502.
Tong, et al., "Biomass into Chemicals: Conversion of Sugars to Furan Derivatives by Catalytic Processes", Applied Catalysts A: General, vol. 385, (2010), pp. 1-13.
Su, et al., "Single-Step Conversion of Cellulose to 5-Hydroxymethylfurfural (HMF), a Versatile Platform Chemical", Applied Catalysts A: General, vol. 361, (2009), pp. 117-122.
Shimizu, et al., "Enhanced Production of Hydroxymethylfurfural from Fructose with Solid Acid Catalysts by Simple Water Removal Methods", Catalysis Communications, vol. 10, (2009), pp. 1849-1853.

* cited by examiner

*Primary Examiner* — Noble Jarrell
*Assistant Examiner* — John Mauro
(74) *Attorney, Agent, or Firm* — Drinker Biddle & Reath LLP

(57) ABSTRACT

The present invention relates to a method for dehydrating a carbohydrate-comprising composition.

29 Claims, 1 Drawing Sheet

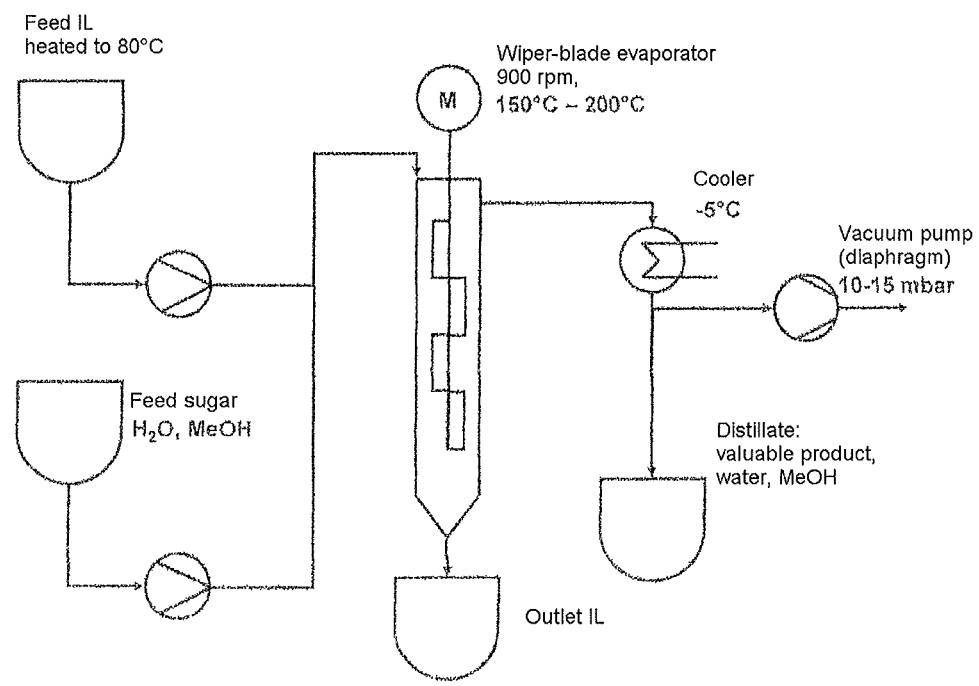

METHOD FOR DEHYDRATING A CARBOHYDRATE-COMPRISING

CROSS-REFERENCE TO RELATED APPLICATIONS

This application claims benefit (under 35 USC 119(e)) of U.S. Provisional Application 61/499,715, filed Jun. 22, 2011, which is incorporated by reference.

The present invention relates to a method for dehydrating a carbohydrate-comprising composition.

In the economic exploitation of valuable materials from biomass feedstocks, especially the dehydration products from diverse carbohydrate sources are ascribed great potential. Hexoses are the most widespread monosaccharides in nature, and especially D-fructose and D-glucose are available in adequate quantities and economically good conditions. The conversion of hexoses to furan products is a particularly highly promising approach. In this case, especially 5-hydroxymethylfurfural (5-HMF), i.e. the dehydration product of hexoses, has a key role. It can serve, inter alia, as starting point for the synthesis of pharmaceuticals, polymers and macrocyclic compounds. Derivatives thereof include, e.g., 2,5-furfuryldiamine, 2,5-furfuryl diisocyanate and 5-hydroxymethylfurfurylidene ester, which can serve for producing polyesters, polyamides and polyurethanes.

Avelino Corma, Sara Iborra, and Alexandra Velty, in Chem. Rev. 2007, 107, 2411-2502, describe diverse chemical routes for converting biomass into chemicals, inter alia under point 2.2.1, the dehydration of monosaccharides, and especially acid-catalyzed dehydration of fructose. Methods in the presence of water have the disadvantage of partial rehydration of the resultant 5-HMF. This disadvantage can be avoided by, e.g., simultaneous extraction of the resultant 5-HMF using an organic solvent, or carrying out the dehydration in an organic solvent. Good yields are achieved, e.g., when the reaction is carried out in DMSO. It is disadvantageous of this variant, however, that DMSO may only be separated off with difficulty from 5-HMF and that toxic sulfur-comprising by-products are formed. Carrying out the reaction in 1-butyl-3-methylimidazolium tetrafluoroborate, i.e. in an ionic solvent, is also mentioned. After a reaction time of three hours at 80° C., 5-HMF could be achieved in 50% yield. By using DMSO as a cosolvent and extending the reaction time to 24 hours, a yield increase to 80% could be achieved.

Xinli Tong, Yang Ma and Yongdan Li, in Applied Catalysis A: General 385 (2010) 1-13, describe the use of sugars for producing furan chemicals, and especially the synthesis of 5-hydroxymethylfurfural (5-HMF), 2,5-furandicarboxylic acid (2,5-FDCA), 2,5-diformylfuran (2,5-DFF), 2,5-bis(hydroxymethyl)furan (2,5-BHF) and 2,5-dimethylfuran (2,5-DMF) from various carbohydrate sources such as fructose, glucose, polysaccharides and biomass feedstocks. Methods based on various catalysts, such as mineral acids, organic acids, solid acids and metal-comprising catalysts, are described.

Yu Su, Heather M. Brown, Xiwen Huang, Xiao-dong Zhou, James E. Amonette and Z. Conrad Zhang, in Applied Catalysis A: General, Volume 361, Issues 1-2, 20 Jun. 2009, pages 117-122, describe the single-stage conversion of cellulose to 5-HMF. A pair of metal chlorides ($CuCl_2$ and $CrCl_2$) dissolved in 1-ethyl-3-methylimidazolium chloride ([EMIM]Cl) catalyzes, at temperatures of 80 to 120° C., the reaction with high purity. In this case cellulose depolymerization is a power of ten more rapid than the acid-catalyzed reaction.

Ken-ichi Shimizu, Rie Uozumi and Atsushi Satsuma, in Catalysis Communications 10 (2009), pages 1849-1853, describe an improved method for producing 5-HMF from fructose in the presence of solid acid catalysts, such as heteropolyacids, zeolites and acid ion-exchange resins, by continuous removal of water from the reaction mixture by a slight reduced pressure.

There continues to be a requirement for economic methods for producing dehydration products from diverse carbohydrate sources. These are intended to make possible rapid, continuous and/or selective production. They are intended, in particular, to be suitable for producing 5-hydroxymethylfurfural (5-HMF) from hexoses and carbohydrate sources comprising hexoses.

Surprisingly, it has been found that this object is achieved by a method in which a carbohydrate-comprising composition that comprises at least one low-boiling solvent and at least one ionic liquid is subjected to a dehydration and simultaneous evaporation of the low-boiling solvent and at least some of the dehydration products formed, and a gaseous discharge from the dehydration/evaporation zone is taken off continuously.

The invention therefore relates to a continuous method for dehydrating a carbohydrate-comprising composition, which comprises i) providing a composition which comprises
   at least one carbohydrate,
   at least one ionic liquid (IL), and
      at least one solvent (LM) that has a boiling point of a maximum of 120° C. under standard pressure (1013 mbar), ii) feeding the composition of step i) into an evaporator and subjecting it to a reaction and evaporation at a temperature in a range from 100 to 300° C. and a pressure of a maximum of 500 mbar, iii) taking off from the evaporator a gaseous discharge which comprises the dehydration product, and taking off a liquid discharge which comprises at least one ionic liquid, iv) condensing the gaseous discharge and subjecting it to a separation with isolation of the dehydration product.

The method according to the invention in embodiments thereof described hereinafter is advantageous with respect to one or more of the following points:
   short residence times in the evaporator;
   continuous method;
   no catalyst required;
   advantageous combination of dehydration in the presence of an ionic solvent and separation by distillation of the resultant dehydration products in a water-comprising, gaseous stream;
   good separation of the resultant dehydration products from the ionic liquid (IL) by gaseous discharge together with the solvent (LM);
   the ionic liquid (IL) present in the liquid discharge is substantially free from the solvent (LM) which is vaporized and discharged in the gaseous state;
   the ionic liquid (IL) present in the liquid discharge is substantially free from the water formed in the dehydration reaction, which water is vaporized and discharged in the gaseous state;
   a deactivation of the ionic liquid (IL) due to accumulation of water is avoided.

BRIEF DESCRIPTION OF THE FIGURE

FIG. 1 shows a device for carrying out the method according to the invention.

A DETAILED DESCRIPTION OF THE INVENTION

Even when the gaseous discharge taken off from the evaporator according to the method according to the invention generally comprises the dehydration products only in the one figure percentage range, the method according to the invention is nevertheless advantageous compared with the known batch methods. Thus the residence time in the evaporator is only in the range of seconds to a few minutes compared with many hours in the known methods. The space-time yield of the method according to the invention is correspondingly high. The short residence time, the rapid removal of the resultant dehydration products in the gas stream and the immediately subsequent condensation enable control of the method with respect to the dehydration product sought as target component. In contrast, the known batch methods lead to constant rehydration and an equilibration of various enolates and therefore to the formation of a complex product spectrum.

The method according to the invention makes possible the production of dehydration products from carbohydrate-comprising starting materials, wherein the use of the customary catalysts known from the prior art for such dehydration reactions can be dispensed with. The carbohydrate-comprising composition used according to the invention for the dehydration is not obligatorily additionally brought into contact with mineral acids, organic acids, acid solid catalysts, such as heteropolyacids, zeolites, and acid ion-exchange resins and metal-comprising catalysts.

The expression "solubilization", in the context of the invention, denotes the conversion into a liquid state and comprises here the generation of solutions of the carbohydrate-comprising starting material and also the conversion into a solubilized state different therefrom. If a polysaccharide, a cellulose material or a lignocellulose material is converted into a solubilized state, the individual polymer molecules need not be necessarily completely surrounded by a solvate sheath. It is critical that the polymer converts into a liquid state owing to the solubilization. Solubilized substances in the context of the invention are therefore also colloidal solutions, microdispersions, gels, etc.

Providing a Carbohydrate-Comprising Composition (Step i)

Preferably, the composition provided in step i) has a content of the carbohydrate-comprising starting material in the range from 1 to 20% by weight, particularly preferably in the range from 2 to 15% by weight, based on the total weight of the composition.

In the context of the present invention, the expression "carbohydrate-comprising composition" comprises compositions which comprise monosaccharides, oligosaccharides, polysaccharides and mixtures thereof. The expression "oligosaccharides" denotes carbohydrates which have two to six monosaccharide units. The expression "polysaccharides" denotes carbohydrates which have more than six monosaccharide units. Typical members of the polysaccharides are, e.g., celluloses, starches and glycogens.

In a first preferred embodiment, the carbohydrate-comprising starting material is selected from mono- and/or oligosaccharides. Especially, the carbohydrate-comprising starting material is selected from mono- and/or disaccharides.

Preferably, the mono- and/or oligosaccharides are selected from
- aldopentoses,
- aldohexoses,
- ketohexoses,
- disaccharides that are derived from aldopentoses, aldohexoses, ketohexoses and mixtures thereof, and
- mixtures thereof.

Particularly preferably, the mono- and/or oligosaccharides are selected from fructose, glucose, sucrose, xylose and mixtures thereof.

A preferred embodiment of the method according to the invention is dehydrating fructose for producing 5-hydroxymethylfurfural (5-HMF).

A preferred embodiment of the method according to the invention is dehydrating sucrose for producing 5-hydroxymethylfurfural (5-HMF).

A preferred embodiment of the method according to the invention is dehydrating xylose for producing furfural.

In a second preferred embodiment, the carbohydrate-comprising starting material is selected from cellulosic starting materials.

Suitable as carbohydrate-comprising starting material for the method according to the invention are, in addition, enzymatic breakdown products of cellulosic or lignocellulosic starting materials.

Ionic liquid (IL)

Ionic liquids, in the context of the present application, denote organic salts which are already liquid at temperatures below 180° C. Preferably, the ionic liquids have a melting point of below 150° C., particularly preferably below 120° C., in particular below 100° C.

Ionic liquids which are already in the liquid state at room temperature are described, for example, by K. N. Marsh et al., Fluid Phase Equilibria 219 (2004), 93-98 and J. G. Huddleston et al., Green Chemistry 2001, 3, 156-164.

Ionic liquids suitable for use in the method according to the invention are described in WO 2008/090155 and WO 2008/090156, which are hereby incorporated herein by reference.

Cations and anions are present in the ionic liquid. In this case, within the ionic liquid, a proton or an alkyl radical can be transferred from the cation to the anion, whereby two neutral molecules result. In the ionic liquid used according to the invention, therefore, an equilibrium of anions, cations and neutral molecules formed therefrom can be present.

Preferred ionic liquids are combinations of nitrogenous cation components (such as imidazolium derivatives) and halogen ions as anions.

Suitable compounds which are suitable for forming the cation of ionic liquids are described, e.g., in DE 102 02 838 A1. These compounds preferably comprise at least one heteroatom such as, e.g., 1 to 10 heteroatoms, which are preferably selected from nitrogen, oxygen, phosphorus and sulfur atoms. Preference is given to compounds which comprise at least one nitrogen atom and optionally additionally at least one further heteroatom different from nitrogen. Preference is given to compounds which comprise at least one nitrogen atom, particularly preferably 1 to 10 nitrogen atoms, in particular 1 to 5 nitrogen atoms, very particularly preferably 1 to 3 nitrogen atoms, and especially 1 or 2 nitrogen atoms. The last-mentioned nitrogen compounds can comprise further heteroatoms such as oxygen, sulfur or phosphorus atoms.

The nitrogen atom is, e.g., a suitable carrier of the positive charge in the cation of the ionic liquid. For the case that the nitrogen atom is the carrier of the positive charge in the cation of the ionic liquid, in the synthesis of the ionic liquids, first, by quaternization at the nitrogen atom, for instance of an amine or nitrogen heterocycle, a cation can be generated. The quaternization can be performed by protonation of the nitrogen atom. Depending on the protonation reagent used, salts having differing anions are obtained. In cases in which it is not possible to form the desired anion as soon as during the quaternization, this can proceed in a further synthesis step. Proceeding, for example, from an ammonium halide, the halide can be reacted with a Lewis acid, wherein a complex anion is formed from halide and Lewis acid. Alternatively thereto, exchange of a halide ion for the desired anion is possible. This can be achieved by adding a metal salt, with precipitation of the metal halide formed, via an ion exchanger, or by displacement of the halide ion by a strong acid (with release of the hydrohalic acid). Suitable methods are described, for example, in Angew. Chem. 2000, 112, pp. 3926-3945 and the literature cited therein.

Preference is given to those compounds that comprise at least one five- to six-member heterocycle, in particular a five-member heterocycle which has at least one nitrogen atom and also possibly one oxygen atom or sulfur atom. Particular preference is given to those compounds that comprise at least one five- to six-member heterocycle which has one, two or three nitrogen atoms, and one sulfur atom or one oxygen atom, very particular preference to those having two nitrogen atoms. Further preference is given to aromatic heterocycles.

Particularly preferred compounds are those that have a molar mass of less than 1000 g/mol, very particularly preferably less than 800 g/mol, and in particular less than 500 g/mol.

Preferred cations are pyridinium ions. These are selected, in particular, from pyridinium, 2-methylpyridinium, 2-ethylpyridinium, 5-ethyl-2-methylpyridinium and 2-methyl-3-ethylpyridinium and also 1-methylpyridinium, 1-ethylpyridinium, 1-(1-butyl)-pyridinium, 1-(1-hexyl)pyridinium, 1-(1-octyl)pyridinium, 1-(1-hexyl)pyridinium, octyl)pyridinium, 1-(1-dodecyl)pyridinium, 1-(1-tetradecyl)pyridinium, 1-(1-hexadecyl)-pyridinium, 1,2-dimethylpyridinium, 1-ethyl-2-methylpyridinium, 1-(1-butyl)-2-methylpyridinium, 1-(1-hexyl)-2-methylpyridinium, 1-(1-octyl)-2-methylpyridinium, 1-(1-dodecyl)-2-methylpyridinium, 1-(1-tetradecyl)-2-methylpyridinium, 1-(1-hexadecyl)-2-methylpyridinium, 1-methyl-2-ethylpyridinium, 1,2-diethylpyridinium, 1-(1-butyl)-2-ethylpyridinium, 1-(1-hexyl)-2-ethylpyridinium, 1-(1-octyl)-2-ethylpyridinium, 1-(1-dodecyl)-2-ethylpyridinium, 9-(1-tetradecyl)-2-ethylpyridinium, 1-(1-hexadecyl)-2-ethylpyridinium, 1,2-dimethyl-5-ethylpyridinium, 1,5-diethyl-2-methylpyridinium, 1-(1-butyl)-2-methyl-3-ethylpyridinium, 1-(1-hexyl)-2-methyl-3-ethylpyridinium 1-(1-octyl)-2-methyl-3-ethylpyridinium, 1-(1-dodecyl)-2-methyl-3-ethylpyridinium, 1-(1-tetradecyl)-2-methyl-3-ethylpyridinium and 1-(1-hexadecyl)-2-methyl-3-ethylpyridinium.

Preferred cations are, in addition, unsubstituted or substituted pyridazinium ions.

Preferred cations are, in addition, unsubstituted or substituted pyrimidinium ions.

Preferred cations are, in addition, unsubstituted or substituted pyrazinium ions.

Preferred cations are, in addition, unsubstituted or substituted imidazolium ions.

Particularly suitable imidazolium ions are 1-methylimidazolium, 1-ethylimidazolium, 1-(1-propyl)imidazolium, 1-(1-allyl)imidazolium, 1-(1-butyl)imidazolium, 1-(1-octyl)-imidazolium, 1-(1-dodecyl)imidazolium, 1-(1-tetradecyl) imidazolium, 1-(1-hexadecyl)-imidazolium, 1,3-dimethylimidazolium, 1,3-diethylimidazolium, 1-ethyl-3-methylimidazolium, 1-(1-butyl)-3-methylimidazolium, 1-(1-butyl)-3-ethylimidazolium, 1-(1-hexyl)-3-methylimidazolium, 1-(1-hexyl)-3-ethylimidazolium, 1-(1-hexyl)-3-butylimidazolium, 1-(1-octyl)-3-methylimidazolium, 1-(1-octyl)-3-ethylimidazolium, 1-(1-octyl)-3-butylimidazolium, 1-(1-dodecyl)-3-methylimidazolium, 1-(1-dodecyl)-3-ethylimidazolium, 1-(1-dodecyl)-3-butylimidazolium, 1-(1-dodecyl)-3-octylimidazolium, 1-(1-tetradecyl)-3-methylimidazolium, 1-(1-tetradecyl)-3-ethylimidazolium, 1-(1-tetradecyl)-3-butylimidazolium, 1-(1-tetradecyl)-3-octylimidazolium, 1-(1-hexadecyl)-3-methylimidazolium, 1-(1-hexadecyl)-3-ethylimidazolium, 1-(1-hexadecyl)-3-butylimidazolium, 1-(1-hexadecyl)-3-octylimidazoliunn, 1,2-dimethylimidazolium, 1,2,3-trimethylimidazolium, 1-ethyl-2,3-dimethylimidazolium, 1-(1-butyl)-2,3-dimethylimidazolium, 1-(1-hexyl)-2,3-dimethylimidazolium, 1-(1-octyl)-2,3-dimethylimidazolium, 1,4-dimethylimidazolium, 1,3,4-trimethylimidazolium, 1,4-dimethyl-3-ethylimidazolium, 3-methylimidazolium, 3-ethylimidazolium, 3-n-propylimidazolium, 3-n-butylimidazolium, 1,4-dimethyl-3-octylimidazolium, 1,4,5-trimethylimidazolium, 1,3,4,5-tetramethylimidazolium, 1,4,5-trimethyl-3-ethylimidazolium, 1,4,5-trimethyl-3-butylimidazolium, 1,4,5-trimethyl-3-octylimidazolium, 1-prop-1-en-3-yl-3-methylimidazolium and 1-prop-1-en-3-yl-3-butylimidazolium. Especially suitable imidazolium ions (IVe) are 1,3-diethylimidazolium, 1-ethyl-3-methylimidazolium, 1-(n-butyl)-3-methylimidazolium.

Preferred cations are, in addition, unsubstituted or substituted pyrazolium ions. Particularly preferred pyrazolium ions are pyrazolium and 1,4-dimethylpyrazolium.

Preferred cations are, in addition, unsubstituted or substituted pyrazolinium ions.

Preferred cations are, in addition, unsubstituted or substituted imidazolinium ions.

Preferred cations are, in addition, unsubstituted or substituted thiazolium ions.

Preferred cations are, in addition, unsubstituted or substituted 1,2,4-triazolium ions.

Preferred cations are, in addition, unsubstituted or substituted pyrrolidinium ions.

Preferred cations are, in addition, unsubstituted or substituted imidazolidinium ions.

Preferred cations are, in addition, unsubstituted or substituted ammonium ions. Examples of the tertiary amines from which the quaternary ammonium ions are derived by quaternization with said radical R are diethyl-n-butylamine, diethyl-tert-butylamine, diethyl-n-pentylamine, diethylhexylamine, diethyloctylamine, diethyl(2-ethylhexyl)-amine, di-n-propylbutylamine, di-n-propyl-n-pentylamine, di-n-propylhexylamine, di-n-propyloctylamine, di-n-propyl(2-ethylhexyl)amine, diisopropylethylamine, diisopropyl-n-propylamine, diisopropylbutylamine, diisopropylpentylamine, diisopropylhexylamine, diisopropyloctylamine, diisopropyl(2-ethylhexyl)amine, di-n-butyl-ethylamine, di-n-butyl-n-propylamine, di-n-butyl-n-pentylamine, di-n-butylhexylamine, di-n-butyloctylamine, di-n-butyl-(2-ethylhexyl)amine, N-n-butylpyrrolidine, N-sec-butylpyrrolidine, N-tert-butyl-pyrrolidine, N-n-pentylpyrrolidine, N,N-dimethylcyclohexylamine, N,N-diethylcyclohexylamine, N,N-di-n-butylcyclohexylamine, N-n-propylpiperidine, N-isopropylpiperidine, N-n-butylpiperidine, N-sec-butylpiperidine, N-tert-butylpiperidine, N-n-pentylpiperidine, N-n-butylmorpholine, N-sec-butylmorpholine, N-tert-butylmorpholine, N-n-pentylmorpholine, N-benzyl-N-ethylaniline, N-benzyl-N-n-propylaniline, N-benzyl-N-isopropylaniline, N-benzyl-N-n-butylaniline, N,N-dimethyl-p-toluidine, N,N-diethyl-p-toluidine, N,N-di-n-butyl-p-toluidine, diethylbenzylamine, di-n-propylbenzylamine, di-n-butylbenzylamine, diethylphenylamine, di-n-propylphenylamine and di-n-butylphenylamine. Preferred tertiary amines are diisopropylethylamine, diethyl-tert-butylamine, diiso-propylbutylamine, di-n-butyl-n-pentylamine, N,N-di-n-butylcyclohexylamine and also tertiary amines of pentyl isomers. Particularly preferred tertiary amines are din-butyl-n-pentylamine, and tertiary amines from pentyl isomers. A further preferred tertiary amine which has three identical radicals is triallylamine.

Preferred cations are, in addition, unsubstituted or substituted guanidinium ions. A very particularly preferred guanidinium ion is N,N,N',N',N'',N''-hexamethylguanidinium.

Preferred cations are, in addition, unsubstituted or substituted cholinium ions.

Preferred cations are, in addition, unsubstituted or substituted cations of 1,5-diaza-bicyclo[4.3.0]non-5-ene (DBN) and 1,8-diazabicyclo[5.4.0]undec-7-ene (DBU).

Preferred cations are, in addition, unsubstituted or substituted phosphonium ions.

Preferred cations are, in addition, unsubstituted or substituted sulfonium ions.

Of the abovementioned heterocyclic cations, the imidazolium ions, imidazolinium ions, pyridinium ions, pyrazolinium ions and pyrazolium ions are preferred. Particular preference is given to the imidazolium ions.

The anion of the ionic liquid is for example selected from
1.) Anions of the formulae: $F^-$, $Cl^-$, $Br^-$ $I^-$, $BF_4^-$, $PF_6^-$, $CF_3SO_3^-$, $(CF_3SO_3^-)_2N^-$, $CF_3CO_2^-$, $CCl_3CO_2^-$, $CN^-$, $SCN^-$, $OCN^-$.
2.) Anions of the formulae: $SO_4^{2-}$, $HSO_4^-$, $SO_3^{2-}$, $HSO_3^-$, $R^cSO_3^-$.
3.) Anions of the formulae: $PO_4^{3-}$, $HPO_4^{2-}$, $H_2PO_4^-$, $R^cPO_4^{2-}$, $HR^cPO_4^-$, $R^cR^dPO_4^-$.
4.) Anions of the formulae: $R^cHPO_3^-$, $R^cR^dPO_2^-$, $R^cR^dPO_3^-$.
5.) Anions of the formulae: $PO_3^{3-}$, $HPO_3^{2-}$, $H_2PO_3^-$, $R^cPO_3^{2-}$, $R^cHPO_3^-$, $R^cR^dPO_3^-$.
6.) Anions of the formulae: $R^cR^dPO_2^-$, $R^cHPO_2^-$, $R^cR^dPO^-$, $R^cHPO^-$.
7.) Anions of the formula $R^cCOO^-$.
8.) Anions of the formulae: $BO_3^{3-}$, $HBO_3^{2-}$, $H_2BO_3^-$, $R^cR^dBO_3^-$, $R^cHBO_3^-$, $R^cBO_3^{2-}$, $B(OR^c)(OR^d)(OR^e)(OR^f)^-1$, $B(HSO_4)_4^-$, $B(R^cSO_4)_4^-$.
9.) Anions of the formulae: $R^cBO_2^{2-}$, $R^cR^dBO^-$.
10.) Anions of the formulae: $HCO_3^-$, $CO_3^{2-}$, $R^cCO_3^-$.
11.) Anions of the formulae: $SiO_4^{4-}$, $H_2SiO_4^{2-}$, $H_2SiO_4^{2-}$, $H_3SiO_4^-$, $R^cSiO_4^{3-}$, $R^cR^dSiO_4^{2-}$, $R^cR^dR^eSiO_4^-$, $HR^c$-$SiO_4^{2-}$, $H_2R^cSiO_4^-$, $HR^cR^dSiO_4^-$.
12.) Anions of the formulae: $R^cSiO_3^{3-}$, $R^cR^dSiO_2^{2-}$, $R^cR^dR^eSiO^-$, $R^cR^dR^eSiO_3^-$, $R^cR^dR^eSiO_2^-$, $R^cR^dSiO_3^{2-}$.
13.) Anions of the formulae:

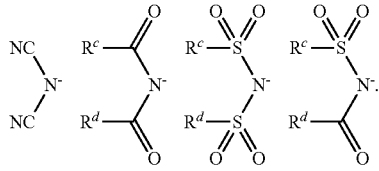

14.) Anions of the formulae:

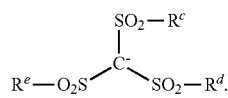

15.) Anions of the formula $R^cO^-$.

16.) Anions of the formulae $HS^-$, $[S_v]^{2-}$, $[HS_v]^-$, $[R^cS]^-$, wherein v is a positive integer from 2 to 10.

The radicals $R^c$, $R^d$, $R^e$ and $R^f$ are, preferably independently of one another,
hydrogen;
unsubstituted or substituted alkyl, preferably unsubstituted or substituted $C_1$-$C_{30}$ alkyl, particularly preferably unsubstituted or substituted $C_1$-$C_{18}$ alkyl which can be interrupted by at least one heteroatom or heteroatom-comprising group;
unsubstituted or substituted aryl, preferably unsubstituted or substituted $C_6$-$C_{14}$ aryl, particularly preferably unsubstituted or substituted $C_8$-$C_{10}$ aryl;
unsubstituted or substituted cycloalkyl, preferably unsubstituted or substituted $C_5$-$C_{12}$ cycloalkyl;
unsubstituted or substituted heterocycloalkyl, preferably unsubstituted or substituted heterocycloalkyl having 5 or 6 ring atoms, wherein the ring, in addition to carbon ring atoms, comprises 1, 2 or 3 heteroatoms or heteroatom-comprising groups;
unsubstituted or substituted heteroaryl, preferably unsubstituted or substituted heteroaryl having 5 to 10 ring atoms, wherein the ring, in addition to carbon ring atoms, comprises 1, 2 or 3 heteroatoms or heteroatom-comprising groups, which are selected from oxygen, nitrogen, sulfur and $NR^a$;
wherein, in anions that comprise a plurality of radicals $R^c$ to $R^f$, also in each case two of these radicals, together with the part of the anion to which they are bound, can be at least one saturated, unsaturated or aromatic ring or a ring system having 1 to 12 carbon atoms, wherein the ring or the ring system can comprise 1 to 5 non-adjacent heteroatoms or heteroatom-comprising groups, that are preferably selected from oxygen, nitrogen, sulfur and $NR^a$, and wherein the ring or the ring system is unsubstituted or can be substituted.

Preferred anions are $Cl^-$, $Br^-$, formate, acetate, propionate, butyrate, lactate, saccharinate, carbonate, hydrogencarbonate, sulfate, sulfite, $C_1$-$C_4$ alkylsulfates, methanesulfonate, tosylate, trifluoroacetate, $C_1$-$C_4$ dialkylphosphates and hydrogensulfate.

Particularly preferred anions are $Cl^-$, $Br^-$, $HCOO^-$, $CH_3COO^-$, $CH_3CH_2COO^-$, carbonate, hydrogencarbonate, sulfate, sulfite, tosylate, $CH_3SO_3^-$ or $CH_3OSO_3^-$.

In particular, the anions are selected from $Cl^-$ and $Br^-$.

Suitable ionic liquids for use in the method according to the invention are commercially available, e.g. under the brand name Basionic® from BASF SE.

Advantageous compounds for use in the method according to the invention are, e.g.:
1-ethyl-3-methylimidazolium chloride (EMIM Cl, Basionic ST 80)
1-ethyl-3-methylimidazolium methanesulfonate (EMIM $CH_3SO_3$, Basionic ST 35), 1-butyl-3-methylimidazolium chloride (BMIM Cl, Basionic ST 70),
1-butyl-3-methylimidazolium methanesulfonate (BMIM $CH_3SO_3$, Basionic ST 78), methylimidazolium chloride (HMIM Cl, Basionic AC 75),
methylimidazolium hydrogensulfate (HMIM $HSO_4$ Basionic AC 39), 1-ethyl-3-methylimidazolium hydrogensulfate (EMIM $HSO_4$ Basionic AC 25), 1-butyl-3-methylimidazolium hydrogensulfate (BMIM $HSO_4$ Basionic AC 28) 1-ethyl-3-methylimidazolium acetate (EMIM Acetate, Basionic BC 01), 1-butyl-3-methylimidazolium acetate (BMIM Acetate, Basionic BC 02).

Particular preference is given to 1-ethyl-3-methylimidazolium chloride, 1-butyl-3-methylimidazolium chloride, methylimidazolium chloride, 1-ethyl-3-methylimidazolium acetate, 1-butyl-3-methylimidazolium acetate and mixtures thereof. Those which are especially suitable are 1-butyl-3-methylimidazolium chloride and methylimidazolium chloride.

Solvents (LM)

The composition provided in step i) comprises at least one solvent (LM) that has a boiling point of a maximum of 120° C. under standard conditions (100° C., 1013 mbar).

The solvent (LM) used in step i) is preferably selected from water and mixtures of water and at least one water-miscible organic solvent.

Preferred water-miscible organic solvents are selected from methanol, ethanol, n-propanol, isopropanol, n-butanol, dioxane, tetrahydrofuran and mixtures thereof.

Preferably, the solvent (LM) used is a water-alcohol mixture, in particular a water-methanol mixture.

Preferably, in step i), as solvent (LM), a mixture of water and at least one water-miscible organic solvent in a weight ratio of 10:90 to 90:10, particularly preferably 25:75 to 75:25, in particular 40:60 to 60:40, is used.

Particularly preferably, in step i), the solvent (LM) used is a mixture of water and at least one alcohol in a weight ratio of 10:90 to 90:10, particularly preferably 25:75 to 75:25, in particular 40:60 to 60:40.

In particular, in step i), the solvent (LM) used is a mixture of water and methanol in a weight ratio of 10:90 to 90:10, particularly preferably 25:75 to 75:25, in particular 40:60 to 60:40.

Preferably, in the carbohydrate-comprising composition provided in step i), the weight ratio of ionic liquid (IL) to solvent (LM) is in a range from 99.5:0.5 to 50:50, particularly preferably 99:1 to 75:25.

For providing the carbohydrate-comprising composition in step i), the carbohydrate-comprising starting material can be brought into intimate contact with the ionic liquid (IL) and/or the solvent (LM). In this process the carbohydrate-comprising starting material is at least partially, preferably completely, solubilized. If necessary, the carbohydrate-comprising starting material is subjected in advance to a pretreatment step for removing insoluble components, and/or insoluble components are separated off from the carbohydrate-comprising composition before it is fed into the evaporator. For providing the carbohydrate-comprising composition in step i), the carbohydrate-comprising starting material and the ionic liquid (IL) and/or the solvent (LM) can be mechanically mixed and stirred up to complete dissolution.

Preferably, for providing the carbohydrate-comprising composition in step i), the at least one ionic liquid (IL) and the at least one solvent (LM) are brought into contact with one another immediately before entry into the evaporator. Immediately before entry into the evaporator means that the time period from the start of the contacting until entry into the evaporator is at most five minutes, particularly preferably at most one minute. The carbohydrate-comprising starting material can, before the start of the contacting, be present solely in the solvent (LM) or solely in the ionic liquid, or partly in the solvent (LM) and partly in the ionic liquid.

Preferably, the ionic liquid (IL), for providing the carbohydrate-comprising composition in step i), is warmed to a temperature above the temperature of the surroundings (23° C.). Preferably, the ionic liquid (IL) used for providing the carbohydrate-comprising composition in step i) has a temperature of at least 50° C., preferably at least 75° C.

In a special embodiment, the method according to the invention serves for dehydrating a mono- and/or oligosaccharide-comprising composition, wherein, in step i):

i1) at least one monosaccharide and/or at least one oligosaccharide is dissolved in a water-alcohol mixture, i2) the solution obtained in step i1) is mixed with at least one ionic liquid (IL), i3) the mixture obtained in step i2) is fed immediately subsequently into the evaporator of step ii).

To feed immediately subsequently into the evaporator means that the time period from the start of the mixing time in step i2) until entry of the mixture into the evaporator is at most five minutes, particularly preferably at most one minute.

Step ii)

In step ii) of the method according to the invention, the composition of step i) is fed into an evaporator and, at elevated temperature and reduced pressure, the carbohydrates present are subjected to a dehydration and simultaneously at least some of the dehydration products formed and the solvent (LM) are vaporized.

As evaporator in step i), preferably an evaporator having a short residence time is used. Advantageously, a low thermal stress of the dehydration products formed is achieved thereby.

Suitable evaporators are, in principle, a device customary therefor, which in the simplest case comprises a container having heatable heat-exchange surfaces. Preferably, a thin-film evaporator or a short-path evaporator is used. Short-path evaporators operate according to the same principle as thin-film evaporators, but have a built-in condenser. The path of the vapors to the condenser is extremely short in the short-path evaporator thereby. A suitable thin-film evaporator is the falling-film evaporator, e.g. a vertical-tube evaporator which can additionally be provided with tube bundles. Preference is given to evaporators having moveable internals in which, e.g., wiper blades generate a thin liquid film on the internal wall of the evaporator (wiped-film evaporator, wiper-blade evaporator). These include thin-film evaporators of the "LUWA"® or "SAM BAY"® types.

The evaporator used according to the invention in step ii) is preferably arranged substantially vertically. The evaporator inlet for feed of the composition from step i) is preferably located in the upper region of the evaporator. Preferably, the evaporator inlet is situated in the upper third, in particular in the upper quarter of the evaporator. The evaporator outlet for removal of the liquid discharge is situated in the lower region of the evaporator. Preferably, the evaporator outlet is situated in the lower third, in particular in the lower quarter of the evaporator. Especially, the evaporator outlet is situated at the bottom end of the evaporator. The composition of step i) is fed into the evaporator in the upper region and forms, on flowing down on the side walls, a film which is heated by a suitable heater. In this process the at least one solvent (LM), which under standard conditions (100° C., 1013 mbar) has a boiling point of a maximum of 120° C., at least partially vaporizes. At the same time, under the reaction conditions in the evaporator, dehydration of the carbohydrate-comprising starting material takes place. From the evaporator, a gaseous discharge is taken off which comprises the dehydration product and at least some of the at least one solvent (LM). The gaseous discharge is preferably discharged in the upper region of the evaporator used according to the invention. In particular, the gaseous discharge is discharged at the top end of the evaporator used according to the invention.

The evaporator can be supplied with heat in a suitable manner, for example with steam.

The temperature in the evaporator is preferably in a range from 100 to 300° C., particularly preferably in a range from 150° C. to 250° C., The pressure in the evaporator is preferably a maximum of 500 mbar. The pressure in the evaporator is particularly preferably in a range from 250 mbar to 0.1 mbar, in particular 100 mbar to 1 mbar.

The residence time in the evaporator, based on the ionic liquid (IL) is preferably in a range from 0.1 second to 2 minutes, particularly preferably 1 second to 1 minute.

Step iii)

From the evaporator, a gaseous discharge is taken off which comprises the dehydration product, and a liquid discharge is taken off which comprises the at least one ionic liquid (IL).

Preferably, the gaseous discharge taken off from the evaporator in step iii) comprises at least 75% by weight, particularly preferably at least 90% by weight, in particular at least 95% by weight, of the solvent (LM), based on the total amount of the solvent (LM) provided in step i).

Preferably, the gaseous discharge taken off from the evaporator in step iii) comprises at least 75% by weight, particularly preferably at least 90% by weight, in particular at least 95% by weight, of the solvent (LM), based on the total amount of the solvent (LM) provided in step i).

Preferably, the gaseous discharge taken off from the evaporator in step iii) comprises at least 0.1% by weight, particularly preferably at least 0.5% by weight, in particular at least 1% by weight, of dehydration products, based on the total weight of the condensed gaseous discharge.

Preferably, the liquid discharge taken off from the evaporator in step iii) comprises at least 90% by weight, particularly preferably at least 95% by weight, especially at least 99% by weight, of the ionic liquid (IL), based on the total amount of the ionic liquid provided in step i).

Preferably, the liquid discharge taken off from the evaporator in step iii) has a water content of a maximum of 5% by weight, particularly preferably a maximum of 1% by weight, in particular a maximum of 0.5% by weight, based on the total weight of the liquid discharge.

The liquid discharge from the reaction zone comprises the proportions of reaction products of the carbohydrate-comprising starting material which are not discharged from the evaporator together with the gaseous discharge. The liquid discharge from the reaction zone comprises, in addition, the unreacted proportions of the carbohydrate-comprising starting material that are not discharged from the evaporator together with the gaseous discharge.

Preferably, the ionic liquid (IL) present in the liquid discharge is used again in step i) of the method according to the invention. In this case the reaction products that are present of the carbohydrate-comprising starting material and the unreacted proportions of the carbohydrate-comprising starting material are generally uncritical.

If desirable, the liquid discharge can be subjected to at least one purification step in order to remove at least in part the residual components present in the ionic liquid (IL). This includes, e.g., extraction with a suitable extraction medium, such as water.

In a further embodiment, the liquid discharge is subjected to a precipitation of at least some of the components present in the ionic liquid by a suitable precipitant. A precipitation is suitable, especially, for removing relatively high-molecular-weight components, e.g. polysaccharides and the relatively high-molecular-weight breakdown products thereof such as cellulose, hemicellulose, etc. Suitable precipitants are known to those skilled in the art.

Step iv)

In step iv) of the method according to the invention, the gaseous discharge from the evaporator is condensed and subjected to a separation, with recovery of the dehydration product.

Suitable condensers are sufficiently known to those skilled in the art, for example heat exchangers such as, e.g., plate heat exchangers, spiral heat exchangers, tube-bundle heat exchangers, U-tube heat exchangers. The condenser is selected and designed in accordance with the requirements. The use of a total condenser is possible, as also a combination of a plurality of condensers connected in series. Preferably, then, the respective downstream condenser in the direction of flow of the gaseous discharge is operated at a lower temperature than the condenser situated further upstream. A fractional condensation of the gaseous discharge from the evaporator can thereby be achieved.

Preferably, the gaseous discharge from the evaporator is cooled in the condenser to a temperature in the range from −30° C. to 70° C., preferably −20° C. to 50° C.

Separation of the condensate can proceed by customary methods known to those skilled in the art. Preferably, the condensate is subjected to a separation by distillation. Suitable devices for separation by distillation comprise distillation columns, such as tray columns, which can be equipped with bubble caps, sieve plates, sieve trays, random packings, ordered packings, valves, side takeoffs, etc., evaporators, such as thin-film evaporators, falling-film evaporators, forced-circulation evaporators, Sambay evaporators, and combinations thereof.

Preferably, the condensate is subjected to separation, with the following streams being obtained:

D1) a stream enriched in dehydrogenated carbohydrates, and
D2) a stream enriched in the solvent (LM).

Optionally, the discharge from the dealkylation zone can be subjected to a separation, with further streams being obtained. If, e.g., in the method according to the invention a mixture is used as solvent, e.g. a mixture of water and at least one water-miscible organic solvent, the fractions D1) and/or D2) can comprise a plurality of components and each can be subjected to a further separation by distillation. Alternatively, for the separation by distillation, columns having side takeoffs, dividing-wall columns, or thermally coupled columns can be used which make possible separation of the condensate into three or more fractions.

Generally, the fraction D1) comprises a main product in an amount of at least 50% by weight, particularly preferably at least 75% by weight, in particular at least 90% by weight. The main product present in the fraction is dependent, inter alia, on the hydrocarbon starting material used. Thus, e.g., when hexoses or a hydrocarbon starting material which comprises predominantly hexose units are used, 5-hydroxy-methylfurfural is obtained as main product.

The resultant dehydration product can (according to desired purity and purpose of use) be used directly or after further work-up and/or purification. This includes, e.g., use for the synthesis of pharmaceuticals, polymers, macrocyclic compounds etc. 5-HMF obtained by the method according to the invention can serve either directly or after derivatization as starting point for the synthesis of pharmaceuticals, polymers and macrocyclic compounds. Suitable 5-HMF derivatives are, e.g., 2,5-furfuryldiamine, 2,5-furfuryl diisocyanate and 5-hydroxymethylfurfurylidene esters, which can be used for producing polyesters, polyamides and polyurethanes.

The solvent (LM) recovered from the condensate or individual components thereof can be reused in step i) of the method according to the invention.

The invention will be described in more detail with reference to the following, non-limiting, examples.

EXAMPLES

FIG. 1 shows a device for carrying out the method according to the invention. Two controllable feeds, of which one serves for feeding a solution of the carbohydrate in a solvent (LM) and one serves for feeding an ionic liquid (IL) are combined and fed into a wiper-blade evaporator. The wiper-blade evaporator used is a Sambay® evaporator made of HC steel having 0.1 m² evaporator surface, four wiper blades and Normag motor. A top outlet is connected to cooler, condensate vessel and diaphragm vacuum pump. In addition, a bottom outlet with collecting vessel is provided.

Example 1

The evaporator is heated to 200° C. internal wall temperature and the wiper-blade speed of rotation is set to 900 rpm. The evaporator is operated at a vacuum of 1 mbar. A feed of 300 g/h of butylmethylimidazolium chloride (BMIM chloride) warmed to 80° C. and a feed of 22.3 g/h of a mixture of fructose/methanol/water (1:1:1, g/g/g) are metered together and simultaneously into the Sambay® evaporator. A gaseous discharge of 421.1 g/h is taken off continuously, condensed in a cooler at −5° C. and collected in a receiver vessel. The condensate is analyzed by HPLC. 2.02 g of 5-HMF/100 g were detected, corresponding to a yield of 8%, based on fructose.

Example 2

The procedure of Example 1 is followed, wherein, as ionic liquid, methylimidazolium chloride (HMIM chloride) is used. The evaporator is heated to 170° C. internal wall temperature. A feed of 300 g/h of HMIM chloride heated to 80° C. and a feed of 44 g/h of a mixture of fructose/methanol/water (1:1:1, g/g/g) are metered together and simultaneously into the Sambay® evaporator. A yield of 10.1% of 5-HMF based on fructose was detected.

The invention claimed is:
1. A continuous method for dehydrating a carbohydrate-comprising composition, which comprises
   i) providing a composition which comprises
      at least one carbohydrate-comprising starting material,
      at least one ionic liquid (IL), and
      at least one solvent (LM) that has a boiling point of a maximum of 120° C. under standard pressure (1013 mbar),
   ii) feeding the composition of step i) into an evaporator and subjecting it to a reaction and evaporation at a temperature in a range from 100 to 300° C. and a pressure of a maximum of 500 mbar, wherein the residence in the evaporator based on the ionic liquid is in a range from 0.1 second to 2 minutes,
   iii) taking off from the evaporator a gaseous discharge which comprises the dehydration product, and taking off a liquid discharge which comprises the at least one ionic liquid, and
   iv) condensing the gaseous discharge and subjecting it to a separation with isolation of the dehydration product.
2. The method according to claim 1, wherein the composition provided in step i) has a content of the carbohydrate-comprising starting material in the range from 1 to 20% by weight, based on the total weight of the composition.
3. The method according to claim 1, wherein the composition provided in step i) has a content of the carbohydrate-comprising starting material in the range from 2 to 15% by weight, based on the total weight of the composition and the carbohydrate-comprising starting material is a monosaccharide or disaccharide or a mixture thereof.
4. The method according to claim 1, wherein the carbohydrate-comprising starting material is monosaccharide or oligosaccharide or a mixture thereof.
5. The method according to claim 4, wherein the monosaccharide or oligosaccharide is selected from the group consisting of
   aldopentose,
   aldohexose,
   ketohexose,
   disaccharide that is derived from aldopentose, aldohexose, ketohexose or a mixture thereof, and
   mixtures thereof.
6. The method according to claim 4, wherein the monosaccharide or oligosaccharide is fructose, glucose, sucrose, xylose or a mixture thereof.
7. The method according to claim 1, wherein the carbohydrate-comprising starting material is selected from cellulosic starting materials and lignocellulosic starting materials.
8. The method according to claim 1, wherein the solvent (LM) is selected from water and mixtures of water and at least one water-miscible organic solvent.
9. The method according to claim 1, wherein the solvent (LM) is a water-alcohol mixture.
10. The method according to claim 1, wherein the solvent (LM) is a water-methanol mixture.
11. The method according to claim 1, wherein, in step i), as solvent (LM), a mixture of water and at least one water-miscible organic solvent in a weight ratio of 10:90 to 90:10 is used.
12. The method according to claim 1, wherein, in the carbohydrate-comprising composition provided in step i), the weight ratio of ionic liquid (IL) to solvent (LM) is in a range from 99.5:0.5 to 50:50.
13. The method according to claim 1, wherein, for providing the carbohydrate-comprising composition in step i), the at least one ionic liquid (IL) and the at least one solvent (LM) are brought into contact with one another immediately before entry into the evaporator.
14. The method according to claim 1, wherein, in step i), as solvent (LM), a mixture of water and at least one water-miscible organic solvent in a weight ratio of 40:60 to 60:40, is used and wherein, in the carbohydrate-comprising composition provided in step i), the weight ratio of ionic liquid (IL) to solvent (LM) is in a range from 99:1 to 75:25.
15. A continuous method for dehydrating a carbohydrate-comprising composition, which comprises
   i) providing a composition which comprises
      at least one carbohydrate-comprising starting material,
      at least one ionic liquid (IL) that is warmed to a temperature of at least 50° C. and
      at least one solvent (LM) that has a boiling point of a maximum of 120° C. under standard pressure (1013 mbar),
   ii) feeding the composition of step i) into an evaporator and subjecting it to a reaction and evaporation at a temperature in a range from 100 to 300° C. and a pressure of a maximum of 500 mbar,
   iii) taking off from the evaporator a gaseous discharge which comprises the dehydration product, and taking off a liquid discharge which comprises the at least one ionic liquid, and iv) condensing the gaseous discharge and subjecting it to a separation with isolation of the dehydration product.

16. A continuous method for dehydrating a carbohydrate-comprising composition, which comprises
   i) providing a composition which comprises
      at least one carbohydrate-comprising starting material,
      at least one ionic liquid (IL) that is warmed to a temperature of at least 75° C. and
      at least one solvent (LM) that has a boiling point of a maximum of 120° C. under standard pressure (1013 mbar),
   ii) feeding the composition of step i) into an evaporator and subjecting it to a reaction and evaporation at a temperature in a range from 100 to 300° C. and a pressure of a maximum of 500 mbar,
   iii) taking off from the evaporator a gaseous discharge which comprises the dehydration product, and taking off a liquid discharge which comprises the at least one ionic liquid, and
   iv) condensing the gaseous discharge and subjecting it to a separation with isolation of the dehydration product.

17. The method according to claim 1 for dehydrating a monosaccharide or oligosaccharide-comprising composition, wherein, in step i):
   i1) at least one monosaccharide and/or at least one oligosaccharide is dissolved in a water-alcohol mixture,
   i2) the solution obtained in step i1) is mixed with at least one ionic liquid (IL),
   i3) the mixture obtained in step i2) is fed immediately subsequently into the evaporator of step ii).

18. The method of claim 1, wherein, in step ii), said evaporator is a thin-film evaporator.

19. The method according to claim 1, wherein, in step ii), said evaporator is a wiper-blade evaporator.

20. The method according to claim 1, wherein, in step ii), the temperature in the evaporator is in a range from 150° C. to 250° C.

21. The method according to claim 1, wherein, in step ii), the pressure in the evaporator is in a range from 250 mbar to 0.1 mbar.

22. The method according to claim 1, wherein, in step ii), the pressure in the evaporator is in a range from 100 mbar to 1 mbar.

23. The method according to claim 1, wherein the gaseous discharge taken off from the evaporator in step iii) comprises at least 75% by weight, of the solvent (LM), based on the total amount of the solvent (LM) provided in step i).

24. The method according to claim 1, wherein the gaseous discharge taken off from the evaporator in step iii) comprises at least 99.5% by weight, of the solvent (LM), based on the total amount of the solvent (LM) provided in step i).

25. The method according to claim 1, wherein the liquid discharge taken off from the evaporator in step iii) comprises at least 90% by weight, of the ionic liquid (IL), based on the total amount of the ionic liquid provided in step i).

26. The method according to claim 1, wherein the liquid discharge taken off from the evaporator in step iii) has a water content of a maximum of 5% by weight, based on the total weight of the liquid discharge.

27. The method according to claim 1, wherein the liquid discharge taken off from the evaporator in step iii) comprises at least 99.5% by weight, of the ionic liquid (IL), based on the total amount of the ionic liquid provided in step i).

28. The method according to claim 1, wherein the liquid discharge taken off from the evaporator in step iii) has a water content of a maximum of 0.5% by weight, based on the total weight of the liquid discharge.

29. The method according to claim 1 for producing
   5-hydroxymethylfurfural from fructose or
   5-hydroxymethylfurfural from sucrose or
   furfural from xylose.

* * * * *